United States Patent
Pfeiffer et al.

(10) Patent No.: US 9,409,839 B2
(45) Date of Patent: Aug. 9, 2016

(54) REMOVAL OF IONIC LIQUIDS BY MEANS OF A KNITTED FABRIC

(71) Applicant: BASF SE, Ludwigshafen (DE)

(72) Inventors: Daniel Pfeiffer, Neustadt (DE); Stefan Bitterlich, Dirmstein (DE)

(73) Assignee: BASF SE (DE)

(*) Notice: Subject to any disclaimer, the term of this patent is extended or adjusted under 35 U.S.C. 154(b) by 258 days.

(21) Appl. No.: 13/937,395

(22) Filed: Jul. 9, 2013

(65) Prior Publication Data

US 2014/0018596 A1    Jan. 16, 2014

Related U.S. Application Data

(60) Provisional application No. 61/670,140, filed on Jul. 11, 2012.

(51) Int. Cl.
*C07C 7/144* (2006.01)

(52) U.S. Cl.
CPC ............. *C07C 7/144* (2013.01); *C07C 2101/14* (2013.01)

(58) Field of Classification Search
None
See application file for complete search history.

(56) References Cited

U.S. PATENT DOCUMENTS

| | | |
|---|---|---|
| 3,271,467 A | 9/1966 | Nakayama |
| 3,406,217 A | 10/1968 | Davison et al. |
| 6,503,465 B1 | 1/2003 | Lin et al. |
| 2003/0109767 A1 | 6/2003 | Vasina et al. |
| 2011/0137097 A1 | 6/2011 | Tschirschwitz et al. |
| 2011/0137098 A1 | 6/2011 | Tschirschwitz et al. |
| 2011/0155632 A1 | 6/2011 | Timken et al. |
| 2011/0155640 A1 | 6/2011 | Timken et al. |

FOREIGN PATENT DOCUMENTS

| | | |
|---|---|---|
| EP | 1503236 A1 | 2/2005 |
| WO | WO-2010062922 A2 | 6/2010 |
| WO | WO-2010074836 A2 | 7/2010 |
| WO | WO-2010075038 A2 | 7/2010 |
| WO | WO-2011069929 A1 | 6/2011 |
| WO | WO-2011069957 A1 | 6/2011 |
| WO | WO-2012104769 A1 | 8/2012 |

OTHER PUBLICATIONS

U.S. Appl. No. 61/438,686, filed Feb. 2, 2011.
U.S. Appl. No. 61/670,130, filed Jul. 11, 2012.
(Continued)

*Primary Examiner* — Tam M Nguyen
(74) *Attorney, Agent, or Firm* — Drinker Biddle & Reath LLP

(57) ABSTRACT

The present invention relates to a process for separating a phase (A) comprising at least one ionic liquid from a phase (B), phase (A) having a higher viscosity than phase (B), comprising the following steps:
a) providing a stream (S1) comprising a dispersion (D1) in which phase (A) is dispersed in phase (B),
b) introducing stream (S1) into a phase separation unit (PT1) comprising a knitted fabric, preferably a knitted glass fiber fabric,
c) separating the dispersed phase (A) from phase (B) in the phase separation unit (PT1),
d) discharging a stream (S2) comprising at least 70% by weight, preferably at least 90% by weight, of phase (A) from the phase separation unit (PT1), and
e) discharging a stream (S3) comprising at least 70% by weight, preferably at least 90% by weight, of phase (B) from the phase separation unit (PT1).

21 Claims, 1 Drawing Sheet

(56) References Cited

OTHER PUBLICATIONS

U.S. Appl. No. 61/670,131, filed Jul. 11, 2012.
U.S. Appl. No. 61/670,132, filed Jul. 11, 2012.
U.S. Appl. No. 61/670,133, filed Jul. 11, 2012.
U.S. Appl. No. 61/670,134, filed Jul. 11, 2012.
U.S. Appl. No. 61/670,135, filed Jul. 11, 2012.
U.S. Appl. No. 61/670,136, filed Jul. 11, 2012.
U.S. Appl. No. 61/670,142, filed Jul. 11, 2012.

REMOVAL OF IONIC LIQUIDS BY MEANS OF A KNITTED FABRIC

CROSS-REFERENCE TO RELATED APPLICATIONS

This patent application claims the benefit of pending U.S. provisional patent application Ser. No. 61/670,140 filed on Jul. 11, 2012, incorporated in its entirety herein by reference.

The present invention relates to a process for separating a phase (A) comprising at least one ionic liquid from a phase (B) using a knitted fabric, especially a knitted glass fiber fabric, phase (A) having a higher viscosity than phase (B).

Ionic liquids are suitable, inter alia, as catalysts for the isomerization of hydrocarbons. A corresponding use of an ionic liquid is disclosed, for example, in WO 2011/069929, where a specific selection of ionic liquids is used in the presence of an olefin for isomerization of saturated hydrocarbons, more particularly for isomerization of methylcyclopentane (MCP) to cyclohexane.

In general, ionic liquids on the one hand and hydrocarbons (or organic phases in general) on the other hand are immiscible or only of very limited miscibility; they form two separate phases. In order to be able to utilize this catalytic action, intensive contact has to be established between organic phase and the ionic liquid. For this purpose, the two phases are frequently mixed in stirred tanks with vigorous stirring to obtain dispersions. Depending on parameters such as the nature of the ionic liquid or of the organic phase or the phase ratio, the dispersion may either be in the form of a dispersion of an ionic liquid in the organic phase or may be a dispersion of the organic phase in the ionic liquid. Irrespective of the specific direction of dispersion, it is a general problem in the case of such dispersions to remove the dispersed phase from the continuous phase after the reaction. A particularly problematic situation is that where the ultrafine droplets of the ionic (d<900 μm) liquid are to be separated from a dispersion in which the ionic liquid is dispersed in the organic phase (ultrafine droplet problem).

For separation of bi- or polyphasic mixtures, especially of dispersions, the use of coalescing filters has long been known. For example, international application PCT/IB2012/050417 (filed Jan. 30, 2012) discloses a process for reducing the water content in pyrolysis gasoline using a coalescing filter manufactured from metal and/or glass fiber. A coalescing filter, however, can be used not just for water removal from mixtures (dispersions) having an organic phase (pyrolysis gasoline), but also for removal of ionic liquids from dispersions comprising an organic phase.

WO 2010/062922 discloses a multistage process for separating an ionic liquid from hydrocarbons using a coalescing filter. The characteristics of the coalescing filter material must be such that it has a stronger affinity for the ionic liquid compared to the hydrocarbons. Suitable coalescing filter materials according to WO 2010/062922 are glass beads, stainless steel, glass fibers, polymer fibers or organic membranes, especially glass fibers. In the coalescing filter, separation of the ionic liquid from the hydrocarbons is accomplished.

It is an object of the present invention to provide a novel process for separating an ionic liquid from an organic phase, the ionic liquid being dispersed in the organic phase.

The object is achieved by a process for separating a phase (A) comprising at least one ionic liquid from a phase (B), phase (A) having a higher viscosity than phase (B), comprising the following steps:

a) providing a stream (S1) comprising a dispersion (D1) in which phase (A) is dispersed in phase (B),
b) introducing stream (S1) into a phase separation unit (PT1) comprising a knitted fabric, preferably a knitted glass fiber fabric,
c) separating the dispersed phase (A) from phase (B) in the phase separation unit (PT1),
d) discharging a stream (S2) comprising at least 70% by weight, preferably at least 90% by weight, of phase (A) from the phase separation unit (PT1), and
e) discharging a stream (S3) comprising at least 70% by weight, preferably at least 90% by weight, of phase (B) from the phase separation unit (PT1).

A BRIEF DESCRIPTION OF THE FIGURES

DETAILED DESCRIPTION OF THE INVENTION

Figure 1:
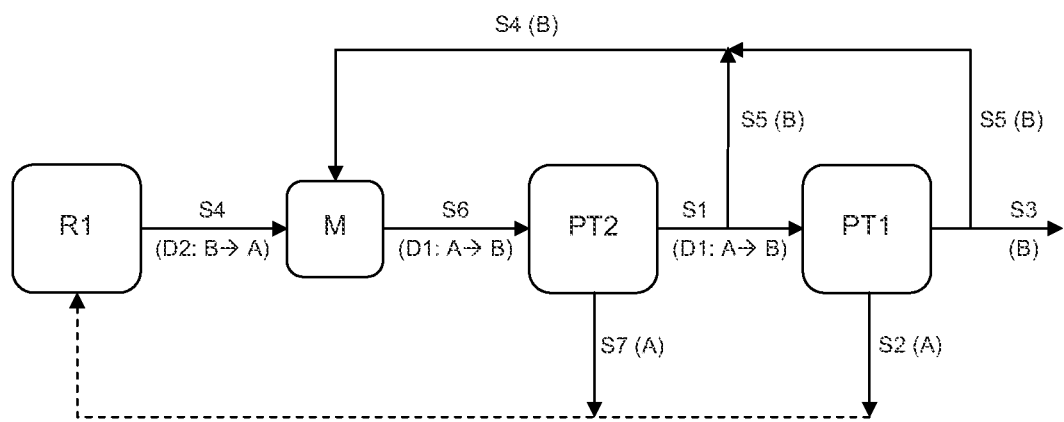
FIG. 1 shows an example of the process according to the invention.

The process according to the invention can advantageously achieve effective separation of ionic liquids from dispersions comprising organic phases, especially from dispersions comprising hydrocarbons. According to the invention, more particularly, the problem of the removal of ionic liquid present in finely dispersed form and/or in small amounts in a dispersion comprising an organic phase can be solved (ultrafine droplet problem).

Compared to the use of coalescing filters, the knitted fabrics used in accordance with the invention, especially the knitted glass fiber fabrics, are notable in that no high pressure drops are observed, and in that the operating costs are much lower for the knitted fabrics. In addition, in the case of the knitted fabrics used in accordance with the invention, no stability problems are found, as frequently observed as a result of the action of organic phases on the materials of the coalescing filters. Thus, the inventive use of the knitted fabrics enables maintenance of the separating performance in the process over a very long period.

In contrast to the use of conventional removal apparatuses such as phase separators, it is possible through the process according to the invention to separate even relatively small amounts (<1% by weight) of ionic liquid from a dispersion comprising an organic phase, especially comprising a hydrocarbon phase; more particularly, this is also true in the case that a direction of dispersion of ionic liquid in organic phase is present. Due to the control of the direction of dispersion of phase (A; ionic liquid) in phase (B; organic phase), a high (rapid) separation rate can be achieved; in addition, phase separators need not necessarily be used in the process. In contrast, in the case of a reverse direction of dispersion—phase (B; organic phase) in phase (A; ionic liquid)—a much lower rate of separation is generally observed; in addition, larger phase separators have to be used.

The process according to the invention can additionally be conducted entirely irrespective of the direction of dispersion in the preceding process steps. If, for example, in a preceding isomerization step, a reverse direction of dispersion with phase (B) in phase (A) is present because, for example, a distinct excess of ionic liquid is used in the isomerization, in a preferred embodiment of the present invention, inversion of the direction of dispersion can be conducted without any problem. The inversion of the direction of dispersion is conducted in accordance with the invention by recycling a stream comprising an excess of organic phase upstream of the phase separation unit (PT1) comprising a knitted fabric and optionally also upstream of the additional phase separation unit (PT2).

The process according to the invention for removal of ionic liquids by means of a knitted fabric is defined in detail hereinafter.

Phase (A) comprises at least one ionic liquid. For example, phase (A) may comprise mixtures of two or more ionic liquids; phase (A) preferably comprises one ionic liquid. As well as the ionic liquid, phase (A) may also comprise further components miscible with the ionic liquid. Such components may, for example, be cocatalysts which are used in isomerization reactions using ionic liquids. A preferred example of such cocatalysts is hydrogen halides, especially hydrogen chloride. In addition, phase (A) may also comprise constituents or decomposition products of the ionic liquids which can form, for example, in the course of the isomerization process, such as aluminum chloride. Preferably, in phase (A), the proportion of ionic liquid is greater than 80% by weight (based on the sum of all components of phase (A)).

Suitable ionic liquids in the context of the present invention are in principle all ionic liquids known to those skilled in the art, provided that they catalyze the reaction to be conducted, for example isomerization. An overview of ionic liquids suitable for catalysis of isomerization reactions can be found, for example, in WO 2011/069929. Preference is given in the context of the present invention to an acidic ionic liquid. The ionic liquid present in phase (A) is preferably an acidic ionic liquid having the composition $K1Al_nX_{(3n+1)}$ where K1 is a monovalent cation, X is halogen and $1<n<2.5$. K1 is preferably an unsubstituted or at least partly alkylated ammonium ion or a heterocyclic (monovalent) cation, especially a pyridinium ion, an imidazolium ion, a pyridazinium ion, a pyrazolium ion, an imidazolinium ion, a thiazolium ion, a triazolium ion, a pyrrolidinium ion, an imidazolidinium ion or a phosphonium ion. X is preferably chlorine or bromine.

The acidic ionic liquid more preferably comprises, as a cation, an at least partly alkylated ammonium ion or a heterocyclic cation and/or, as an anion, a chloroaluminate ion having the composition $Al_nCl_{(3n+1)}$ where $1<n<2.5$. The at least partly alkylated ammonium ion preferably comprises one, two or three alkyl radicals (each) having 1 to 10 carbon atoms. If two or three alkyl substituents are present with the corresponding ammonium ions, the respective chain length can be selected independently; preferably, all alkyl substituents have the same chain length. Particular preference is given to trialkylated ammonium ions having a chain length of 1 to 3 carbon atoms. The heterocyclic cation is preferably an imidazolium ion or a pyridinium ion.

The acidic ionic liquid especially preferably comprises, as a cation, an at least partly alkylated ammonium ion and, as an anion, a chloroaluminate ion having the composition $Al_nCl_{(3n+1)}$ where $1<n<2.5$. Examples of such particularly preferred ionic liquids are trimethylammonium chloroaluminate and triethylammonium chloroaluminate.

In the context of the present invention, phase (A) has a higher viscosity than phase (B). The viscosity of phase (A) is preferably at least 0.1 mPas and especially at least 20 mPas higher than that of phase (B). In the context of the present invention, a first characteristic of phase (B) is that it has a lower viscosity than phase (A). For example, phase (B) may be an organic phase. Phase (B) preferably comprises at least one hydrocarbon. Phase (B) more preferably comprises, as the hydrocarbon, cyclohexane or a mixture of cyclohexane with at least one further hydrocarbon selected from methylcyclopentane (MCP), n-hexane, isohexane, n-heptane, iso-heptane or dimethylcyclopentane. Phase (B) especially preferably comprises a mixture of cyclohexane, MCP and at least one further hydrocarbon.

In the context of the present invention, in step a), a stream (S1) comprising a dispersion (D1) in which phase (A) is dispersed in phase (B) is provided. The direction of dispersion (i.e. the information as to which phase is in disperse form in the respective other phase) can be determined by examining a sample, optionally after addition of a dye which selectively stains one phase, under a transmitted light microscope.

Dispersion (D1) can be produced by methods known to those skilled in the art; for example, such a dispersion can be obtained by vigorous stirring of the components present in the respective phases. Such an operation can take place, for example, in the course of an isomerization process of hydrocarbon using an ionic liquid. Dispersion (D1) is (as explained in detail hereinafter) preferably withdrawn as the upper phase from a phase separation apparatus, which is especially preferably connected downstream of an apparatus in which a reaction catalyzed by the ionic liquid is conducted and in which the ionic liquid and the organic phase are contacted with stirring. In the dispersion (D1), phases (A) and (B) may be present in any desired ratios relative to one another, provided that phase (A) is dispersed in phase (B). Preferably, phase (A) is present to a maximum extent of 10% by weight, especially to a maximum extent of 5% by weight, in stream (S1) in dispersion (D1) (based in each case on the amount of phase (B)).

In step b) of the invention, stream (S1) is introduced into a phase separation unit (PT1) comprising a knitted fabric, preferably a knitted glass fiber fabric. Suitable knitted fabrics, especially knitted glass fiber fabrics, are known to those skilled in the art; they are commercially available, for example, from Rhodius (Germany). The preferred knitted glass fiber fabrics are glass staple fibers having a fiber diameter between 0.1 and 0.6 mm, preferably between 0.14 to 0.3 mm. The knitted fabric comprises essentially wound (glass staple) fiber mats having a packing density between 100 and 800 kg/m³, preferably 150 to 500 kg/m³, more preferably 200 to 400 kg/m³.

As evident, for example, from the working example of the present invention, such a knitted fabric is usually integrated into a larger apparatus, in the present case into the phase separation unit (PT1). The phase separation unit (PT1) comprising a knitted fabric is preferably a phase separator, more preferably a downstream phase separator, i.e. an apparatus connected downstream of a further phase separator.

In step c), the dispersed phase (A) is separated from phase (B) in the phase separation unit (PT1). The performance of the separation as such—the action of the knitted fabric giving phases (A) and (B) separated from one another—by means of a knitted fabric is known to those skilled in the art.

According to step d), in the process of the invention, a stream (S2) comprising at least 70% by weight, preferably at least 90% by weight, of phase (A) is discharged from the phase separation unit (PT1). Especially preferably, only small amounts of phase (B), if any, are present in stream (S2) (<1% by weight). The above figures in % by weight are based on the corresponding amounts present in stream (S1).

In step e), a stream (S3) comprising at least 70% by weight, preferably at least 90% by weight, of phase (B) is discharged from the phase separation unit (PT1). Especially preferably, only small amounts of phase (A), if any, are present in stream (S2) (<1% by weight). The above figures in % by weight are based on the corresponding amounts present in stream (S1).

The stream (S1) provided in step a) is preferably obtained from an (additional) phase separation unit (PT2) connected upstream of the phase separation unit (PT1) comprising a knitted fabric. This phase separation unit (PT2) is preferably a phase separator; more preferably the phase separator of the phase separation unit (PT2) does not comprise any knitted fabric. In addition, the phase separation unit (PT2) is preferably connected downstream of a reaction apparatus or a cascade of reaction apparatuses. This reaction apparatus or cascade of reaction apparatuses preferably comprises apparatus which are suitable for conducting an isomerization of hydrocarbons in the presence of at least one ionic liquid as a catalyst.

In a preferred embodiment of the present invention, in addition to the above-described steps a) to e), the following additional steps f) to k) are conducted, these being defined as follows:

f) discharging a stream (S4) from the reaction apparatus or the cascade of reaction apparatuses, (S4) comprising a dispersion (D2) in which phase (B) is dispersed in phase (A), g) introducing a stream (S5) comprising at least 70% by weight, preferably at least 90% by weight, of phase (B), into stream (S4), stream (S5) being recycled from step k), preference being given to mixing streams (S4) and (S5) by means of a return element or of a static mixer, h) to form a stream (S6) comprising a dispersion (D1) in which phase (A) is dispersed in phase (B), i) introducing stream (S6) into the phase separation unit (PT2) connected upstream of the phase separation unit (PT1), j) separating stream (S6) in the phase separation unit (PT2) into a stream (S1) according to step a), and into a stream (S7) comprising at least 70% by weight, preferably at least 90% by weight, of phase (A), k) removing a portion of stream (S1) and/or a portion of stream (S3) according to step e) as stream (S5) and recycling stream (S5) to step g).

In the context of the present invention, stream (S5) which is introduced into stream (S4) in step g) can be formed from a portion of stream (S1). Alternatively, stream (S5) can also be formed from a portion of stream (S3). Optionally, stream (S5) can also be formed from different or identical portions of streams (S1) and (S3). Stream (S5) is preferably formed from a portion of stream (S1). In general less than 50% of streams (S1) and/or (S3) are removed as stream (S5) and recycled into stream (S4). However, it is also conceivable that, at least temporarily, larger amounts or the corresponding streams are even recycled completely. The recycling of portions of streams (S1) and/or (S3) as stream (S5) and the associated introduction of stream (S5) into stream (S4) preferably achieves inversion of the direction of dispersion in stream (S4). Inversion of the direction of dispersion means that stream (S4) comprises a dispersion (D2) in which phase (B) is dispersed in phase (A). The amount and/or the rate of introduction of stream (S5) in step g) are selected so as to form a stream (S6) comprising dispersion (D1) in which phase (A) is dispersed in phase (B). If an additional phase separation unit (PT2), especially a phase separator without knitted fabric, is connected upstream of the phase separation unit (PT1), the proportion of phase (A) in dispersion (D1) is reduced further, which has an advantageous effect on the separation performance of the phase separation unit (PT1).

Preferably, in step g), stream (S5) is introduced into stream (S4) in a stirring or mixing apparatus in which stream (S6) according to step h) is formed.

It is additionally preferable that the phase ratio of phase (A) to phase (B) in dispersion (D1) present in stream (S6) is ≤3 [kg/kg], preferably ≤0.9 [kg/kg].

It is additionally preferable that stream (S4) is obtained from an isomerization, preferably from an isomerization in the presence of an ionic liquid, especially an isomerization of methylcyclopentane (MCP) to cyclohexane in the presence of an ionic liquid.

It is additionally preferable that, in step k), stream (S5) is removed from stream (S1) outside the phase separation unit (PT2).

Optionally, stream (S7) removed from the phase separation unit (PT2) according to step j) and/or stream (S2) discharged from the phase separation unit (PT1) according to step d), each of which comprises phase (A), can be recycled into the reaction apparatus or the cascade of reaction apparatuses. Optionally, stream (S7) and/or stream (S2) can also be recycled to another point in the process according to the invention, for example into a mixing or stirring apparatus, in order to control the concentration of phase (A) in dispersion (D1).

In the context of the present invention, cyclohexane is preferably isolated from stream (S3). Processes and apparatuses for removal of cyclohexane from stream (S3), especially when it is a hydrocarbon mixture, are known to those skilled in the art. Optionally, prior to the removal of the cyclohexane, further purification steps (for example a wash with an aqueous and/or alkaline phase) can be conducted, these being known to those skilled in the art.

FIG. 1 once again illustrates the process according to the invention (in a configuration) of the preferred embodiment described above. According to FIG. 1, the process is performed by recycling a portion both from stream (S1) and from stream (S3) as stream (S5) into stream (S4). For better understanding, FIG. 1 states the main components present in each of the streams in brackets below each of them. For streams (S1), (S4) and (S6), the respective expression in brackets also includes the direction of dispersion of the respective dispersions, the arrow expressing the direction of dispersion. This means that, for example, dispersion (D2) present in stream (S4) has a phase (B) dispersed in phase (A). In FIG. 1, stream (S5) is introduced into stream (S4) in a mixing apparatus (M). The broken line indicates that streams (S7) and/or (S2) can optionally also be recycled into the reaction apparatus or a cascade of reaction apparatuses (R1).

EXAMPLES

For the experiment, the following substances are used:
Phase (A):
ionic liquid (IL) with the composition $(CH_3)_3NH\ Al_nCl_{3n+1}$ where n=1.82 according to elemental analysis (also referred to as IL phase).
Phase (B):
hydrocarbon mixture with the composition (also referred to as organic phase)
methylcyclopentane 20% by weight
cyclohexane 50% by weight
hexane 28%
isohexanes (technical mixture) 2% by weight
For the experiments described, phases (A) and (B) are used in a ratio of 0.1 kg(A)/kg(B).

Figure 2:
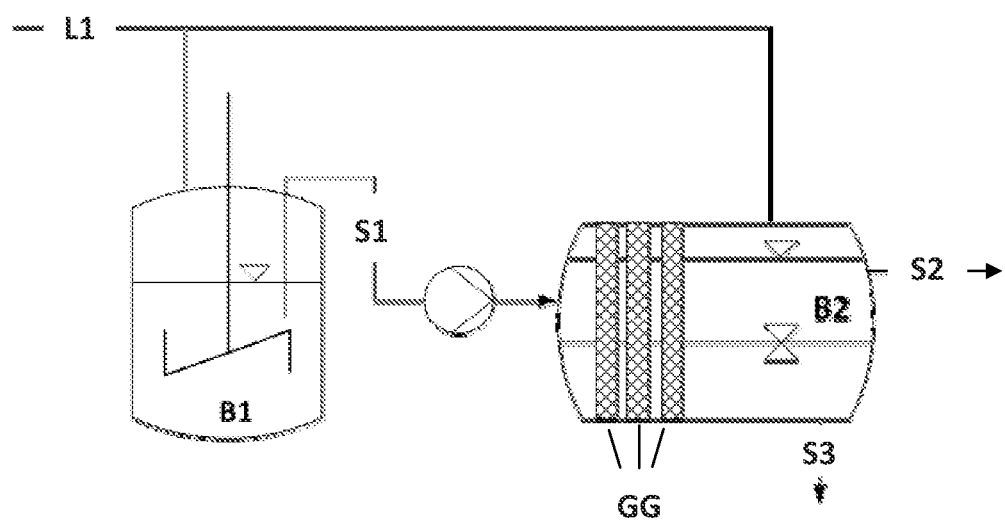
FIG. 2 shows an experimental arrangement for a filtration test with a knitted glass fiber fabric.

1. Filtration Test with a Knitted Glass Fiber Fabric
The experimental arrangement is shown in the figure according to FIG. 2:
Vessel (B1) (6 l glass stirred vessel, internal diameter 200 mm with a 6-blade pitched-blade stirrer, diameter 70 mm) is initially charged with a biphasic mixture of (A) and (B), with (A) dispersed in (B). (B1) is (like (B2) too) connected to a nitrogen-conducting gas line (L1) which is kept at atmospheric pressure.

From (B1), liquid can be pumped by means of a gear metering pump into the vessel (B2) (volume 220 ml, internal diameter 40 mm), which has been provided with three successive knitted glass fiber fabrics which fill the entire internal cross section (manufacturer: Rhodius, dimensions: diameter 40 mm, thickness 10 mm, 400 kg/m$^3$).

All vessels are equipped with a jacket and are kept at 40° C. by means of a heat carrier oil circulated through a laboratory thermostat during the experiments described below.

The contents of (B1) are stirred initially at 1200 rpm for 10 min, then the stirrer is switched off. After a settling phase of 10 min, a constantly turbid upper phase is found. Elemental analysis of the upper phase gives a nitrogen content of 240 ppm. By means of the pump, with a delivery rate of 14.3 l/h (corresponding to a superficial velocity on the knitted fabric of 11.37 m$^3$/m$^2$/h), upper phase is conducted from (B1) to (B2). From (B2), via stream (S3), a clear organic phase is obtained, which, according to elemental analysis, has a nitrogen content of 7 ppm by weight.

The invention claimed is:

1. A process for separating a phase (A) comprising at least one ionic liquid from a phase (B) comprising at least one hydrocarbon, phase (A) having a higher viscosity than phase (B), comprising the following steps:
    a) providing a stream (S1) comprising a dispersion (D1) in which phase (A) is dispersed in phase (B),
    b) introducing stream (S1) into a phase separation unit (PT1) comprising a knitted fabric,
    c) separating the dispersed phase (A) from phase (B) in the phase separation unit (PT1),
    d) discharging a stream (S2) comprising at least 70% by weight of phase (A) from the phase separation unit (PT1), and
    e) discharging a stream (S3) comprising at least 70% by weight of phase (B) from the phase separation unit (PT1).

2. The process according to claim 1, wherein the knitted fabric is a knitted glass fiber fabric.

3. The process according to claim 1, wherein in step d) the stream (S2) comprises at least 90% by weight of phase (A) or in step e) the stream (S3) comprises at least 90% by weight of phase (B).

4. The process according to claim 1, wherein the viscosity of phase (A) is at least 0.1 mPas higher than that of phase (B).

5. The process according to claim 1, wherein phase (B) comprises, as the hydrocarbon, cyclohexane or a mixture of cyclohexane with at least one further hydrocarbon selected from methylcyclopentane (MCP), n-hexane, isohexane, n-heptane, isoheptane or dimethylcyclopentane.

6. The process according to claim 1, wherein the ionic liquid present in phase (A) is an acidic ionic liquid having the composition $K1Al_nX_{(3n+1)}$ where K1 is a monovalent cation, X is halogen and $1<n<2.5$.

7. The process according to claim 6, wherein the acidic ionic liquid comprises, as a cation, an at least partly alkylated ammonium ion or a heterocyclic cation or, as an anion, a chloroaluminate ion having the composition $Al_nCl_{(3n+1)}$ where $1<n<2.5$.

8. The process according to claim 1, wherein the phase separation unit (PT1) comprising a knitted fabric is a phase separator.

9. The process according to claim 1, wherein stream (S1) is obtained from a phase separation unit (PT2) which is connected upstream of the phase separation unit (PT1) comprising a knitted fabric and which is in turn connected downstream of a reaction apparatus or a cascade of reaction apparatuses.

10. The process according to claim 9, wherein the phase separation unit (PT2) is a phase separator.

11. The process according to claim 9 comprising the following additional steps:
    f) discharging a stream (S4) from the reaction apparatus or the cascade of reaction apparatuses, (S4) comprising a dispersion (D2) in which phase (B) is dispersed in phase (A),
    g) introducing a stream (S5) comprising at least 70% by weight of phase (B), into stream (S4), stream (S5) being recycled from step k),
    h) to form a stream (S6) comprising a dispersion (D1) in which phase (A) is dispersed in phase (B),
    i) introducing stream (S6) into the phase separation unit (PT2) connected upstream of the phase separation unit (PT1),
    j) separating stream (S6) in the phase separation unit into a stream (S1) according to step a), and into a stream (S7) comprising at least 70% by weight of phase (A),
    k) removing a portion of stream (S1) or a portion of stream (S3) according to step e) as stream (S5) and recycling stream (S5) to step g).

12. The process according to claim 11, wherein, in step g), stream (S5) is introduced into stream (S4) in a stirring apparatus in which stream (S6) according to step h) is formed.

13. The process according to claim 11, wherein the phase ratio of phase (A) to phase (B) in dispersion (D1) present in stream (S6) is ≤3 [kg/kg].

14. The process according to claim 13, wherein the phase ration is ≤0.9 [kg/kg].

15. The process according to claim 11, wherein stream (S4) is obtained from an isomerization.

16. The process according to claim 15, wherein the isomerization is an isomerization of methylcyclopentane (MCP) to cyclohexane in the presence of an ionic liquid.

17. The process according to claim 11 wherein, in step k), stream (S5) is removed from stream (S1) outside the phase separation unit.

18. The process according to claim 1, wherein cyclohexane is isolated from stream (S3).

19. The process according to claim 1, wherein phase (A) is present to a maximum extent of 5% by weight in stream (S1) in dispersion (D1), based on the amount of phase (B).

20. The process according to claim 9, wherein the phase separation unit (PT2) does not comprise any knitted fabric.

21. A process for separating a phase (A) comprising at least one ionic liquid from an organic phase (B), phase (A) having a higher viscosity than phase (B), comprising the following steps:
    a) providing a stream (S1) comprising a dispersion (D1) in which phase (A) is dispersed in phase (B),
    b) introducing stream (S1) into a phase separation unit (PT1) comprising a knitted fabric,
    c) separating the dispersed phase (A) from phase (B) in the phase separation unit (PT1),
    d) discharging a stream (S2) comprising at least 70% by weight of phase (A) from the phase separation unit (PT1), and
    e) discharging a stream (S3) comprising at least 70% by weight of phase (B) from the phase separation unit (PT1).

* * * * *